US00PP26911P3

(12) United States Plant Patent

Klemm et al.

(10) Patent No.: US PP26,911 P3

(45) Date of Patent: Jul. 5, 2016

(54) *PETUNIA* PLANT NAMED 'KLEPH13239'

(50) Latin Name: *Petunia hybrida*
Varietal Denomination: KLEPH13239

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 61 days.

(21) Appl. No.: 14/120,064

(22) Filed: Apr. 21, 2014

(65) Prior Publication Data

US 2015/0305217 P1 Oct. 22, 2015

(51) Int. Cl.
*A01H 5/02* (2006.01)

(52) U.S. Cl.
USPC ..... Plt./356.23

(58) Field of Classification Search
USPC ..... Plt./356.1, 356.23
See application file for complete search history.

*Primary Examiner* — June Hwu

(74) *Attorney, Agent, or Firm* — Barbara Campbell; Bethany R. Roahrig; Cochran Freund & Young, LLC

(57) ABSTRACT

A new *Petunia* plant particularly distinguished by orange-red flowers having greyed-orange throats with darker greyed-orange veins, a medium-compact form, and an upright-mounding plant habit, is disclosed.

2 Drawing Sheets

Genus and species: *Petunia hybrida.*
Variety denomination: 'KLEPH13239'.

BACKGROUND OF THE NEW PLANT

The present invention comprises a new and distinct variety of *Petunia*, botanically known as *Petunia hybrida*, and hereinafter referred to by the variety name 'KLEPH13239'. 'KLEPH13239' originated from a cross-pollination conducted in July 2010 in Latina, Italy between the female *Petunia* variety 'Surprise Orange Twist' and the male *Petunia* variety SUN SPUN 'Red'.

The seeds from the cross were sown and plants were grown in a greenhouse for evaluation, where an individual plant designated 'KLEPH13239' was selected from the group in April 2011 of plants in Latina, Italy, having orange-red flowers with greyed-orange throats and darker greyed-orange veins. In April 2011, 'KLEPH13239' was first vegetatively propagated by terminal tip cuttings and meristem tissue culture. 'KLEPH13239' was found to reproduce true to type in successive generations of asexual propagation via tissue culture and terminal tip cuttings.

SUMMARY

The following are the most outstanding and distinguishing characteristics of this new variety when grown under normal horticultural practices in Stuttgart, Germany and Latina, Italy.

1. Orange-red flowers having greyed-orange throats with darker greyed-orange veins;
2. A medium-compact form; and
3. An upright-mounding plant habit.

DESCRIPTION OF THE PHOTOGRAPHS

This new *Petunia* plant is illustrated by the accompanying photographs of plants grown in a greenhouse in Stuttgart, Germany. The colors shown are as true as can be reasonably obtained by conventional photographic procedures.

DESCRIPTION OF THE NEW VARIETY

Figure 1:
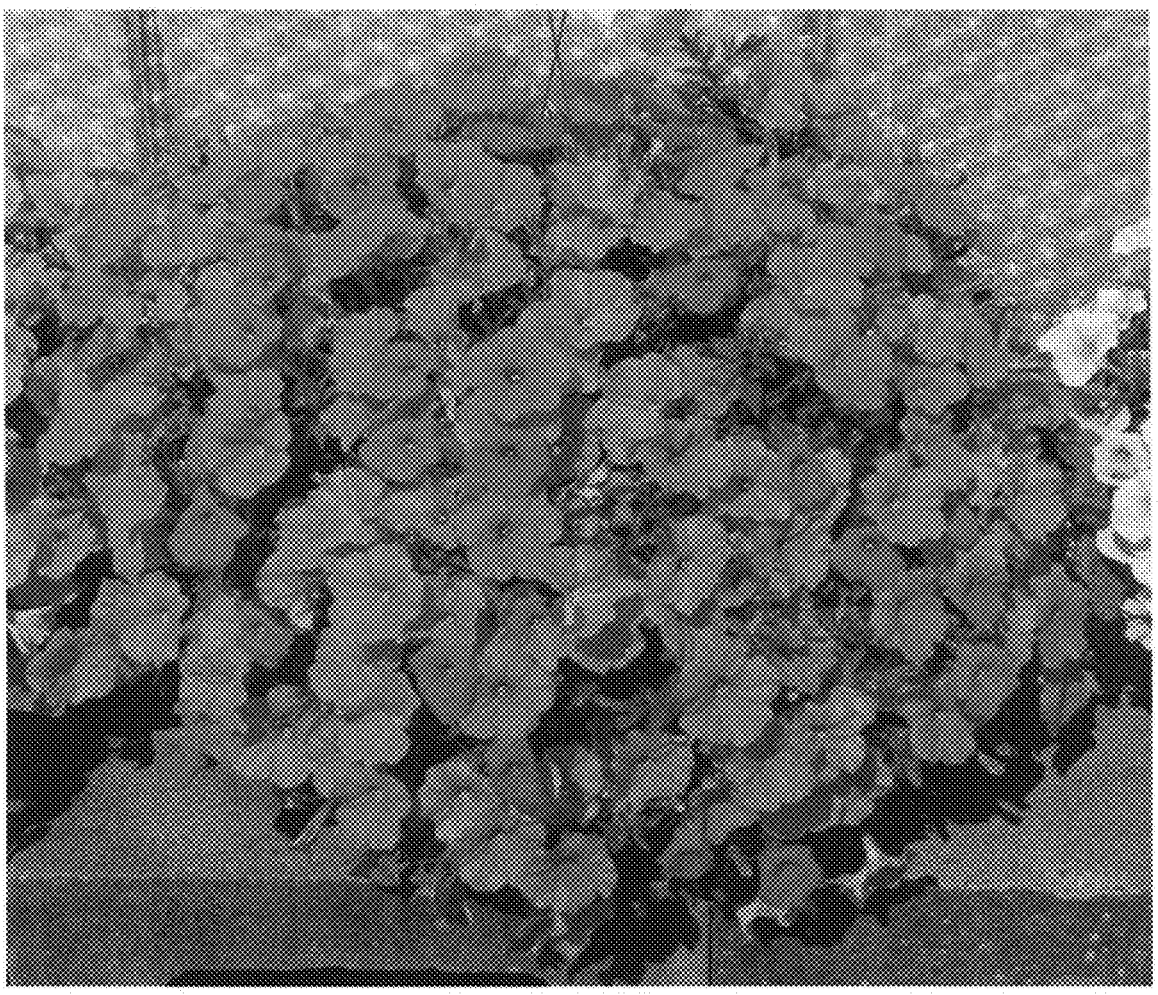
FIG. 1 shows a photograph taken in July 2013 of a 5-month-old plant grown in a basket.
Figure 2:
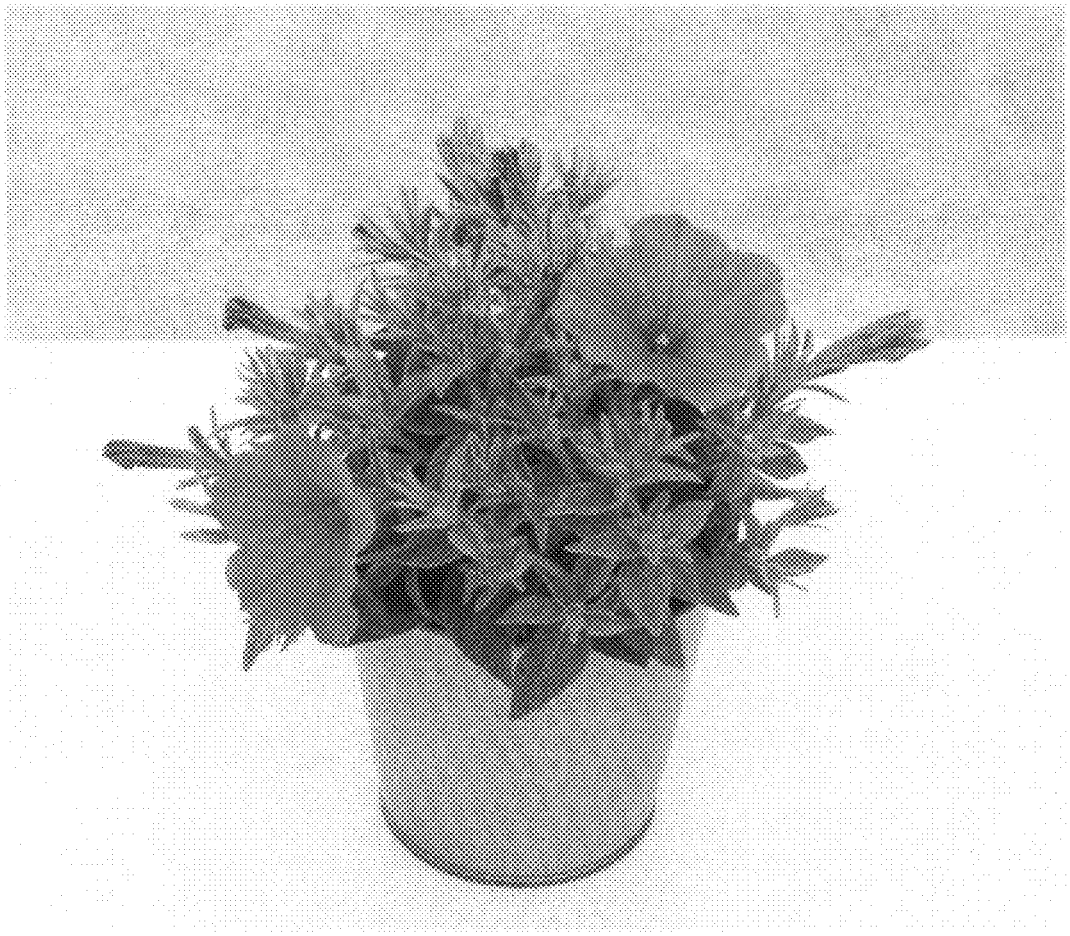
FIG. 2 shows a photograph taken in May 2013 of a 3-month-old plant grown in a pot.

The following detailed descriptions set forth the distinctive characteristics of 'KLEPH13239'. The data which define these characteristics were collected from asexual reproductions carried out in Latina, Italy. Data was collected on plants grown 14-weeks from cultivation from potting in a plastic greenhouse in Latina, Italy in March 2014. Color references are to The R.H.S. Colour Chart of The Royal Horticultural Society of London (R.H.S.), 5$^{th}$ edition (2007).

Classification:
- *Family.*—Solanaceae.
- *Botanical.—Petunia hybrida.*
- *Common.—Petunia.*
- *Designation.*—'KLEPH13239'.

Parentage:
- *Female parent.*—The female *Petunia* variety 'Surprise Orange Twist'.
- *Male parent.*—The male *Petunia* variety SUN SPUN 'Red'.

Plant:
- *Form.*—Medium-compact.
- *Habit.*—Upright-mounding.
- *Height (from top of soil).*—About 12.0 cm.
- *Width (horizontal plant diameter).*—About 24.0 cm.
- *Propagation.*—Terminal tip cuttings and meristem tissue culture.
- *Time to produce a finished flowering plant.*—14 to 15 weeks in the winter and 7 weeks in the spring.
- *Time to initiate and develop roots.*—2 to 3 weeks.

*Root description*.—Moderate density, moderate branching, white roots.

Stems:

*Average number* (*basal*).—About 18.

*Length of basal branches* (*from the base of the stem to the tip*).—About 12.0 cm.

*Internode length*.—1.0 cm to 2.5 cm.

*Diameter of branches* (*from midpoint*).—0.3 cm.

*Stem color*.—RHS 144B.

*Anthocyanin*.—Absent.

*Texture*.—Pubescent.

Leaves:

*Arrangement*.—Alternate at the base of the stems, opposite on the flower stems.

*Length*.—3.0 cm to 3.5 cm.

*Width*.—1.5 cm to 2.0 cm.

*Shape*.—Elliptic.

*Apex*.—Acute.

*Base*.—Attenuate.

*Margin*.—Entire.

*Immature and mature leaf color*.—Upper surface: RHS N137D. Lower surface: RHS 138B.

*Texture* (*both upper and lower surfaces*).—Pubescent.

*Venation pattern*.—Arcuate.

*Venation color*.—Upper surface: RHS 137B. Lower surface: RHS 138B.

*Petioles*.—Length: 0.3 cm. Diameter: 0.2 cm. Color: RHS 137B. Texture: Pubescent.

Flower buds:

*Shape*.—Irregular oblong.

*Length*.—About 3.0 cm.

*Diameter*.—0.3 cm.

*Color at tight bud*.—RHS 176A.

*Texture*.—Slightly pubescent.

Inflorescence:

*Blooming habit* (*flowering season*).—Continuous flowering during summer time.

*Inflorescence type*.—Cymose.

*Number of flowers per node*.—1.

*Lastingness of individual blooms on the plant*.—7 to 10 days.

*Fragrance*.—Absent.

*Flowers*.—Arrangement: Composed of 5 petals fused at the base. Shape: Funnel-form. Diameter (flower face): 6.0 cm. Depth (total length of flower): 6.0 cm. Throat/Funnel: Length: 2.0 cm. Diameter (at opening): 1.3 cm. Texture (both inner and outer surfaces): Smooth, glabrous. Throat color, inner surface: RHS 177B. Throat color, outer surface: RHS 177D with RHS 177A veins. Petals: Apex: Mucronate. Base: Fused. Margin: Entire. Strength of waviness: Weak. Degree of lobation: Medium-weak. Immature color: Upper surface: RHS 46B. Lower surface: RHS 182B to RHS 182C. Mature color: Upper surface: RHS 34A. Lower surface: RHS 182C to RHS 182D. Calyx arrangement: Actinomorphic, composed of 5 sepals. Sepals: Color: Upper surface: RHS N137D. Lower surface: RHS 138B. Length: 2.0 cm. Width: 0.4 cm. Shape: Linear. Apex: Acute. Base: Attenuate. Margin: Entire. Texture (both upper and lower surfaces): Pubescent.

*Pedicels*.—Color: RHS 144A. Length: 3.5 cm. Diameter: 0.15 cm. Texture: Pubescent.

Reproductive organs:

*Stamens*.—Quantity: 5. Shape: Needle with elliptic head. Filament: Length: 1.0 cm to 1.2 cm. Diameter: About 0.02 cm. Color: RHS 36C. Anther: Shape: Elliptic. Color: RHS 27B. Length: 0.3 cm. Diameter: 0.2 cm. Pollen: Color: RHS 157B. Amount: Moderate.

*Pistils*.—Quantity per flower: 1. Length: 1.8 cm. Stigma color: RHS 157A. Style color: RHS 160D.

Fruit and seed set: No fruit and seed set observed to date.

Disease and pest/insect resistance: No disease and pest/insect resistance observed.

COMPARISON WITH PARENTAL LINES AND KNOWN VARIETY

'KLEPH13239' is a distinct variety of *Petunia* and is distinguished from its parents as described in Table 1.

TABLE 1

Comparison with Parental Lines

| Characteristic | 'KLEPH13239' | Female Parent 'Surprise Orange Twist' | Male Parent SUN SPUN 'Red' |
|---|---|---|---|
| Flower color | Orange-red with a greyed-orange throats and darker greyed-orange veins | Brilliant orange with darker veins and a dark throat | Red |

'KLEPH13239' is a distinct variety of *Petunia* and is most similar to the commercial *Petunia* variety SUN SPUN 'Red'. Differences between the varieties are described in Table 2.

TABLE 2

Comparison with Similar Variety

| Characteristic | 'KLEPH13239' | SUN SPUN 'Red' |
|---|---|---|
| Flower color | Orange-red with greyed-orange throats and darker greyed-orange veins | Red |

We claim:

1. A new and distinct variety of *Petunia* plant designated 'KLEPH13239' as illustrated and described herein.

* * * * *